United States Patent [19]
Hase et al.

[11] Patent Number: 5,196,544
[45] Date of Patent: Mar. 23, 1993

[54] CYCLIC OLIGOIMINOETHERS

[75] Inventors: Brigitte Hase, Erkrath; Horst-Juergen Krause, Duesseldorf, both of Fed. Rep. of Germany; William Fristad, Santa Rosa, Calif.

[73] Assignee: Henkel Kommanditgesellschaft auf Aktien, Duesseldorf-Holthausen, Fed. Rep. of Germany

[21] Appl. No.: 776,247

[22] Filed: Jan. 16, 1992

[30] Foreign Application Priority Data

May 16, 1989 [DE] Fed. Rep. of Germany ....... 3915874

[51] Int. Cl.$^5$ .................. C07D 263/14; C07D 265/08
[52] U.S. Cl. ...................... 548/238; 528/73; 544/88; 544/96; 548/237
[58] Field of Search ............................ 544/96; 548/238

[56] References Cited

U.S. PATENT DOCUMENTS

| | | | |
|---|---|---|---|
| 3,438,943 | 4/1969 | Miranda et al. | 548/238 |
| 3,763,177 | 10/1973 | Tomalia et al. | 548/237 |
| 3,996,237 | 12/1976 | Tomalia | 548/238 |
| 4,138,545 | 2/1979 | Emmons et al. | 544/96 |
| 4,378,357 | 3/1983 | Miller et al. | 548/238 |

FOREIGN PATENT DOCUMENTS

| | | | |
|---|---|---|---|
| 0273368 | 7/1988 | European Pat. Off. | |
| 90-14341 | 11/1990 | PCT Int'l Appl. | 548/238 |

OTHER PUBLICATIONS

Chem. Abstr. vol. 115 entry 50476y abstracting German 3915874 (1990).
Chem. Abstr. vol. 115 Entry 9615e Abstracting German 3924164 (1991).

*Primary Examiner*—Donald G. Daus
*Attorney, Agent, or Firm*—Ernest G. Szoke; Wayne C. Jaeschke; Norvell E. Wisdom, Jr.

[57] ABSTRACT

This invention concerns polyiminoethers of general formula (I) in which A is an aliphatic, aromatic or araliphatic group containing 4 to 40 carbon atoms and n free valencies at various carbon atoms, x may assume values of 0 to 40, n has a value of 2, 3 or 4, Z is either a direct bond or the group $CR^5R^6$, the substituents $R^1$ to $R^6$ independently of one another are H, alkyl or aryl containing up 8 carbon atoms, the substituent $R^7$ is hydrogen, methyl or ethyl and Q is a phenylene group, which may be substituted by one or two methyl groups, or the group —CHR—M—, where R is selected from the group consisting of H, alkyl or alkenyl and M is selected from the group consisting of alkylene, alkenylene, arylene and alkarylene, and the parts R and M of the molecule independently of one another contain 0 to 12 carbon atoms and, in addition, may be substituted by a $C_{1-3}$ alkoxy group. These compounds are made from polyisocyanates of formula $A(NCO)_n$ and cyclic monoiminoethers containing hydroxyl groups and are suitable for subsequent processing to polymers.

19 Claims, No Drawings

CYCLIC OLIGOIMINOETHERS

BACKGROUND OF THE INVENTION

1. Field of the Invention

This invention relates to new compounds which contain a 5- or 6-membered cyclic iminoether group two, three or four times in the molecule, to a process for their production and to their use.

2. Statement of Related Art

Cyclic polyiminoethers are known as valuable intermediate products and, according to EP 273 368, DE 20 29 524 and DE 35 39 593 for example, are used for the production of plastics, resins and adhesives. Hitherto, however, an obstacle to the wide-scale application of these intermediate products has been the lack of a simple and, at the same time, high-yield synthesis process for polyiminoethers.

DESCRIPTION OF THE INVENTION

A new group of cyclic oligoiminoethers, which are alternately called polyiminoethers has now been hereafter, found which can be produced both easily and in high yields from readily available starting materials. They are the subject of the present invention.

The polyiminoethers according to the invention correspond to general formula I

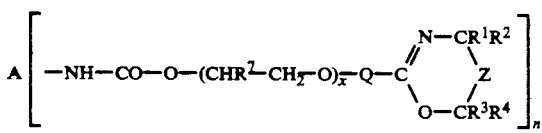

in which A is an aliphatic, aromatic or araliphatic group containing 4 to 40 carbon atoms and n free valencies at various carbon atoms, x may assume values of 0 to 40, n has a value of 2, 3 or 4, Z is either a direct bond or the group $CR^5R^6$, the substituents $R^1$ to $R^6$ independently of one another are H, alkyl or aryl containing up 8 carbon atoms, the substituent $R^7$ is hydrogen, methyl or ethyl and Q is a phenylene group, which may be substituted by one or two methyl groups, or the group —CHR—M—, where R is selected from the group consisting of H, alkyl or alkenyl and M is selected from the group consisting of alkylene, alkenylene, arylene and alkarylene, and the parts R and M of the molecule independently of one another contain 0 to 12 carbon atoms and, in addition, may be substituted by a $C_{1-3}$ alkoxy group.

The new polyiminoethers may be synthesized in a substantially quantitative yield from polyisocyanates corresponding to formula II $$A(-NCO)_n \qquad II$$

by reaction with iminoethers corresponding to formula

III

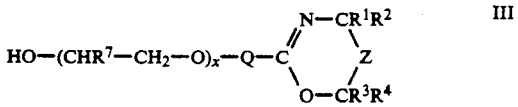

the new polyiminoethers being formed in a single stage by reaction of the hydroxyl groups of III with the isocyanate groups in II.

The smooth course of this reaction is all the more surprising inasmuch as it is known that cyclic iminoethers substituted in the 2-position react to isocyanates as bi-functional reagents with exocyclic displacement of the double bond on the iminoether ring (see, for example, R. Nehring et al., *Liebigs Ann. Chem.* 698, 167 (1966)). Instead of this reaction, which would necessarily lead to products of high molecular weight where polyisocyanates corresponding to formula II are used with cyclic aminoethers, definite low molecular weight polyiminoethers corresponding to formula I are obtained in a substantially quantitative yield in the present case. Providing no more than the equivalent quantity of isocyanate, based on hydroxyl groups, is used, hydroxyl-free cyclic iminoethers additionally present are themselves hardly attacked.

The reaction between the isocyanates II and the iminoethers III takes place smoothly under the conditions typically used in the reaction of alcohols with isocyanates, i.e. temperatures between about room temperature and about 160° C. and reaction times of about 1 to 10 hours. However, the reaction conditions may also be distinctly above or below these limits, depending on the reactivity of the isocyanates. The reaction may be carried out in the presence of suitable aprotic solvents, for example aromatic hydrocarbons, chlorinated hydrocarbons, esters or ketones, or even in the absence of solvents and, generally, in the absence of moisture. Polymerizable substances which do not react under the reaction conditions applied, for example cyclic iminoethers free from hydroxyl groups, (meth)acrylates and other vinyl compounds, may also be used as solvents for the synthesis of the cyclic polyiminoethers, depending on the purpose for which they are to be subsequently used. The catalysts typically used for the reaction of alcohols with isocyanates, above all tin compounds, such as dibutyl tin dilaurate, or tertiary amines, such as 1,4-diazabicyclo-[2,2,2]-octane, may be added to accelerate the urethane-forming reaction. The progress of the reaction may be followed by determination of the unreacted isocyanate, for example by reaction with excess dibutylamine in toluene and back-titration with HCl. Since the reaction is quantitative, even where equivalent quantities of the reactants are used, i.e. n moles of iminoether (III) per mole isocyanate (II), working up of the synthesis mixtures is extremely easy or may even be omitted altogether.

According to the invention, cyclic polyiminoethers corresponding to formula Ia

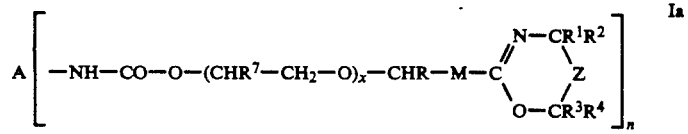

which are prepared from polyisocyanates (II) and n moles of iminoethers corresponding to formula IIIa

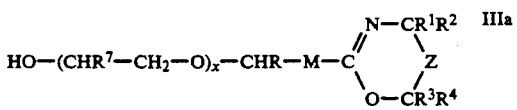

are preferred. In these formulae, R and M are as defined above.

According to the invention, other preferred polyiminoethers are those in which at least four of the substituents $R^1$ to $R^6$ are hydrogen atoms and the others consist of $C_{1-3}$ alkyl. Other preferred polyiminoethers are those prepared from 2-(hydroxyalkyl)-2-oxazolines (III, Z=direct bond). Of these polyiminoethers, those having the following substitution patterns are particularly preferred:

$R^1$=CH$_3$, $R^2$-$R^4$=H;
$R^1$ and $R^2$=CH$_3$, $R^3$ and $R^4$=H;
$R^3$=CH$_3$, C$_2$C$_5$ or phenyl; $R^1$, $R^2$ and $R^4$=H.

Finally, those polyiminoethers in which Z is the methylene group or a direct bond and all the substituents $R^1$ to $R^4$ are hydrogen atoms are particularly preferred.

Other preferred iminoethers are the bis-iminoethers (I, n=2) which are formed with diisocyanates, of which the bis-iminoethers prepared from 1,6-hexamethylene diisocyanate; 2,4-tolylene diisocyanate; 4,4'- and/or 2,4'-diphenylmethane diisocyanate, 4,4'-dicyclohexylmethane diisocyanate, m-tetramethyl xylylene diisocyanate and isophorone diisocyanate are particularly preferred.

The diisocyanates and polyisocyanates of formula II used as starting material are well-known compounds in the chemical field which are normally prepared from the corresponding amines with COCl$_2$ In part A of the molecule, they preferably contain 6 to 26 carbon atoms. In addition to the diisocyanates mentioned above, N,N',N''-tris-(ω-isocyanatohexyl)-biuret and 2,2,4-trimethyl hexamethylene-1,6-diisocyanate are mentioned by way of example. Further information in this regard can be found in reference books, such as Kirk-Othmer, *Encyclopedia of Chemical Technology*, 3rd Edition, Vol. 23, page 586 (1984).

The iminoethers (III) required in accordance with the invention may also be obtained in known manner, for example by cyclization of derivatives of hydroxycarboxylic acids HO—CHR—M—CO$_2$H, for example by the processes according to earlier patent applications EP 8811090.5, DE-P 39 14 133, DE-P 39 14 155 and DE-P 39 14 159 or by Litt and and Levy's process (*J. Polym. Sci.* A1, 6, 1883 (1968) Or by other typical synthesis processes for cyclic iminoethers (for example DE 1 445 642 or S. Kobayaski and T. Saegusa in *Ring-opening Polymerization*, Vol. 2, London 1984, pages 762 et seq.). Iminoethers (III), in which x has a value of greater than 0, may be obtained from derivatives of hydroxycarboxylic acids corresponding to formula HO—(CH-R$^7$—CH$_2$—O—)$_x$—CHR—M—CO$_2$H which, in turn, may be obtained in known manner, for example by reaction of the derivatives of hydroxycarboxylic acids HO—CHR—M—CO$_2$H with x moles of butylene oxide, propylene oxide or, preferably, ethylene oxide. However, these iminoethers may also be prepared by initially preparing iminoethers corresponding to formula III with x=0 as described above and alkoxylating these iminoethers in the usual way with x moles butylene oxide, propylene oxide or, preferably, ethylene oxide. x preferably has a value of 0 to 10 and, more preferably, the value 1 or 0. The iminoethers derived from ricinoleic acid, dihydroricinoleic acid, caprolactone or from epoxidized unsaturated fatty acids ring-opened with monohydric lower alcohols are particularly preferred. In the first case, the 2-alkyl moiety of the cyclic iminoether III consists of the 11-hydroxy-8-heptadecenyl moiety, in the second case of the 11-hydroxyheptadecyl moiety, in the third case of the 5-hydroxypentyl moiety and, in the last case, preferably of a linear C$_{17}$ or C$_{21}$ alkyl moiety internally vicinally substituted by a hydroxyl group and an alkoxyl group (preferably containing 1 to 3 carbon atoms).

The new polyiminoethers are versatile intermediate products. They may be used with particular advantage in processes for the production of optionally cross-linked polymers, in which case the polyiminoethers are used on their own, but preferably in conjunction with other low molecular weight or polymeric starting materials. Accordingly, the present invention also relates to this use of the new polyiminoethers.

Examples of the use of the bis-, tris- and tetrakis-iminoethers according to the invention include the crosslinking polymerization with polycarboxylic acids according to DE 35 39 593 or the production of resins by reaction with polyfunctional alcohols or amines in accordance with EP 273 368.

EXAMPLES

1. A mixture of 323 g (1 mole) of 2-(11-hydroxy-8-heptadecenyl)-2-oxazoline (technical, from ricinoleic acid) and 125 g (0.5 mole) 4,4'-diphenylmethane diisocyanate (DESMODUR ® M, a product of Bayer AG, Leverkusen) was heated for 4 hours to 80° C. in the absence of moisture. Thereafter, no more isocyanate could be detected by titration with dibutylamine. The product was a pale yellowish viscous liquid.

The following structure of the product was confirmed by the H-NMR spectrum:

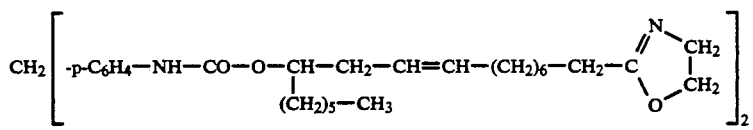

NMR (1% in CDCl$_3$, delta scale)
0.8–1.0 ppm (t; 6 H)
1.1–2.4 ppm (5m; about 52 h)
3.7–3.9 ppm (t+s; 6 H)
4.1–4.3 ppm (t; 4 H)
4.7–4.9 ppm (q; 2 H)
5.2–5.6 ppm (m; 4 H)
6.6–6.7 ppm (s; 2 H)
7.0–7.4 ppm (2 d; 8 H)

2. A mixture of 323 g (1 mole) of 2-(11-hydroxy-8-heptadecenyl)-2-oxazoline (technical) and 84 g (0.5 mole) of 1,6-hexamethylene diisocyanate (DESMODUR ® H, Bayer AG) was heated for 10 hours to 80° C. in the absence of moisture. Thereafter, no more isocyanate could be detected. The product solidified on cooling to form a wax-like solid. The following structure of the product was confirmed by the H-NMR spectrum:

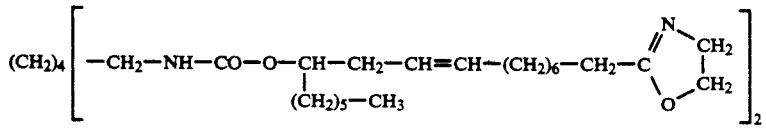

NMR (1% in CDCl₃, delta scale)
0.8–1.0 ppm (t; 6 H)
1.1–2.4 ppm (5 m, about 60 H)
3.0–3.3 ppm (q; 4 H)
3.7–3.9 ppm (t; 4 H)
4.1–4.3 ppm (t; 4 H)
4.5–4.9 ppm (t+s; 4 H)
5.2–5.6 ppm (m; 4 H)

3. 157 g (1 mole) of 2-(5-hydroxypentyl)-2-oxazoline and 125 g (0.5 mole) of 4,4'-diphenylmethane diisocyanate (DESMODUR ® M, a product of Bayer AG) was heated with stirring to 80° C. in the absence of moisture until the reaction was complete (4 hours). The product solidified on cooling to form a solid. The structure of the product was confirmed by the H-NMR spectrum:

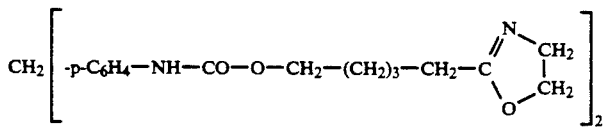

NMR (1% in CDCl₃, delta scale)
1.3–1.8 ppm (2 m; about 12 H)
2.2–2.4 ppm (t; 4 H)
3.7–4.0 ppm (t+s; 6 H)
4.0–4.3 ppm (2 t; 8 H)
6.9–7.0 ppm (s; 2 H)
7.0–7.4 ppm (2 d; 8 H)

4. 411 g (1 mole) of 2-[12,13-(hydroxy,methoxy)-heneicosyl]-2-oxazoline (derivative of epoxidized erucic acid, technical, ring-opened with methanol) and 125 g (0.5 mole) of 4,4'-diphenylmethane diisocyanate (Desmodur ® M) were thoroughly mixed in the absence of moisture and the resulting mixture was heated for 4 hours to 80° C. Thereafter, no more isocyanate could be detected.

After cooling, the product was a yellowish, highly viscous liquid.

The structure of the product was confirmed by the H-NMR spectrum:

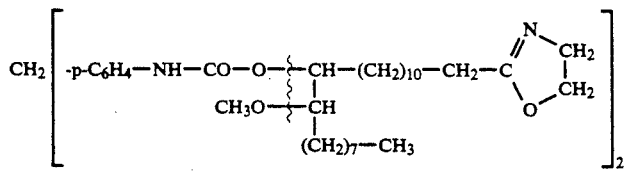

NMR (1% in CDCl₃, delta scale)
0.8–1.0 ppm t, 6 H)
1.1–1.7 ppm (3m, about 68 H)
2.2–2.4 ppm (t, 4 H)
3.1–3.3 ppm (m, 2 H)
3.3–3.5 ppm (s, 6 H)
3.7–3.9 ppm (t+s, 6 H)
4.1–4.3 ppm (t, 4 H)
4.8–5.0 ppm (m, 2 H)
6.7–6.9 ppm (2s, 2 H)
7.0–7.4 ppm (2d, 8 H)

5. 323 g (1 mole) of 2-(11-hydroxy-8-heptadecenyl)-2-oxazoline (technical) and 158 g (0.33 mole) of N,N',N''-tris(ω-isocyanatohexyl)-biuret (Desmodur ® N) were stirred for 8 hours at 80° C. in the absence of moisture. Thereafter, no more isocyanate could be detected. After cooling, the product was a light yellow, viscous liquid.

The structure of the product was confirmed by the H-NMR spectrum.

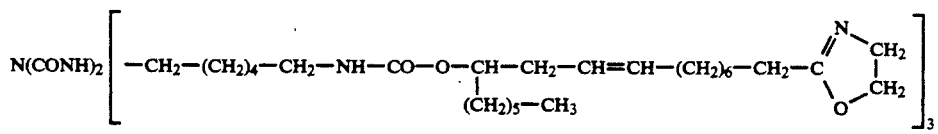

NMR (1% in CDCl₃, delta scale)
0.8–1.0 ppm (t; 9H)
1.1–2.4 ppm (5m; about 102 H)
3.0–3.4 ppm (2m; 10 H)
3.6–3.9 ppm (m+t; 2+6 H)
4.1–4.3 ppm (t; 6 H)
4.6–4.9 ppm (m; 6 H)
5.2–5.6 ppm (m; 6 H)
7.1–7.6 ppm (m, 2 H)

6. 325 g (1 mole) of 2-(11-hydroxyheptadecyl)-2-oxazoline (technical) and 87 g (0.5 mole) of 2,4-tolylene diisocyanate (DESMODUR ® T) were stirred for 12 hours at 80° C. in the absence of moisture. Thereafter, no more isocyanate could be detected. The product was a yellowish viscous liquid. The structure of the product was confirmed by the H-NMR spectrum:

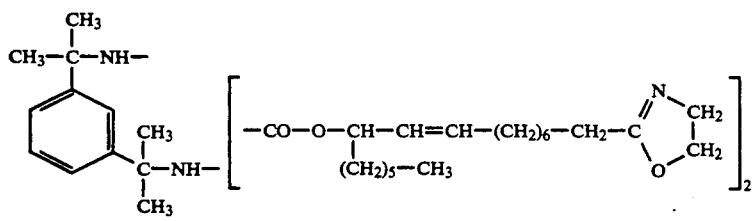

NMR (1% in CDCl₃, delta scale)
0.8-1.0 ppm t 6 H)

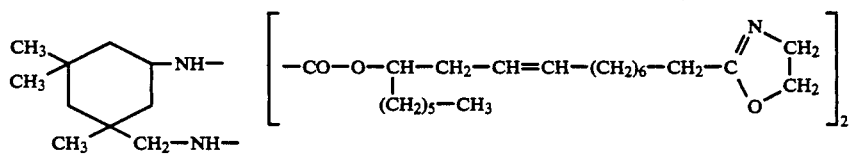

1.1-1.7 ppm (2m; about 56 H)
2.1-2.4 ppm (s+t; 3+4 H)
3.7-3.9 ppm (t; 4 H)
4.1-4.3 ppm (t; 4 H)
4.7-4.9 ppm (m; 2 H)
6.4 ppm (s; 1 H)
6.7 ppm (s; 1 H)
7.0-7.4 ppm (2d; 2 H)
7.8 ppm (s; 1 H)

7. 337 g (1 mole) of 2-(11-hydroxy-8-heptadecenyl)-2-oxazine (technical, prepared in accordance with earlier patent application DE P 39 14 255) were stirred with 125 g (0.5 mole) of 4,4-diphenylmethane diisocyanate (DESMODUR ® M Bayer AG) for 5 hours at 80° C. in the absence of moisture. Thereafter, no more isocyanate could be detected. The product was a yellowish viscous liquid. The structure of the product was confirmed by the H-NMR spectrum:

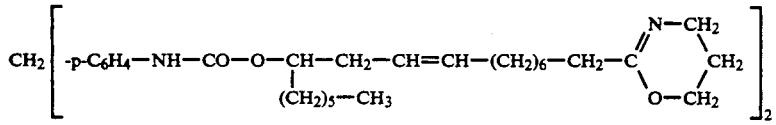

NMR (1% in CDCl₃, delta scale)
0.8-1.0 ppm (t; 6 H)
1.1-2.4 ppm (5m; about 56 H)
3.2-3.4 ppm (t; 4 H)
3.8-3.9 ppm (s; 2 H)
4.0-4.3 ppm (t; 4 H)
4.7-5.0 ppm (m; 2 H)
5.2-5.6 ppm (m; 4 H)
6.8 ppm (s; 2 H)
7.0-7.4 ppm (2d; 8 H)

8. 323 g (1 mole) of 2-(11-hydroxy-8-heptadecenyl)-2-oxazoline (technical) and 111 g (0.5 mole) of isophorone diisocyanate (VEBA Chemie) were stirred for 8 hours at 80° C. in the absence of moisture. Thereafter, no more isocyanate could be detected. The product was a light yellow viscous liquid. The structure of the product was confirmed by the H-NMR spectrum:

NMR (1% in CDCl₃, delta scale)
0.8-1.9 ppm (6m, about 61 H)
1.9-2.4 ppm (2m; 4+8 H)
2.8-3.0 ppm (m; 2 H)
3.2-3.3 ppm (m; 1 H)
3.7-3.9 ppm (t; 4 H)
4.1-4.3 ppm (m; 4 H)
4.3-4.5 ppm (m; about 2 H)
4.6-4.9 ppm (m; 2 H)
5.2-5.6 ppm (m; 4 H)

9. 41.4 g (0.2 mole) of 2-(p-hydroxyethoxyphenyl)-2-oxazoline (Mp.: 146° C., prepared from p-(2-hydroxyethoxy)benzoic acid {Beilstein E II 10, page 93} and ethanolamine by the process described in earlier German patent application P 39 14 133) Were mixed under nitrogen at room temperature with 26.2 g (0.1 mole) of methylene-bis-(4-cyclohexylisocyanate) (DESMODUR ® W, Bayer AG) and the resulting mixture was heated for 5 hours to 180° C. Thereafter, no more isocyanate could be detected. The product solidified on cooling to form a yellowish wax-like solid. The structure of the product was confirmed by the H-NMR spectrum:

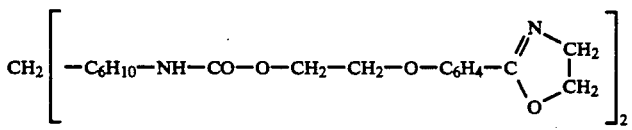

NMR (1% in CDCl₃, delta scale)
0.8-2.1 ppm (4m; 20 H)
3.3-3.9 ppm (2m; 2 H)
3.9-4.6 ppm (3m; 16 H)
4.6-5.1 ppm (2d; 2 H)
6.8-7.0 ppm (m; 4 H)

7.8-8.0 ppm (m; 4 H)

10. A mixture of 323 g (1 mole) of 2-(11-hydroxy-8-heptadecenyl)-2-oxazoline (technical) and 131 g of methylene-bis-(4-cyclohexylisocyanate) (DESMODUR ® W, Bayer AG) was heated for 48 hours to 80° C. in the absence of moisture. After cooling, the product was a yellowish viscous liquid. The structure of the product was confirmed by the H-NMR spectrum:

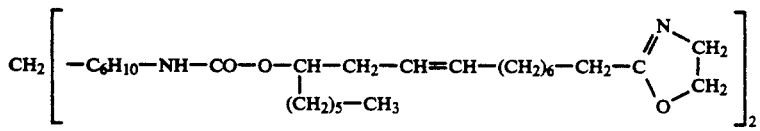

NMR (1% in CDCl₃, delta scale)
0.5-0.95 ppm (t; 6 H)
0.95-1.9 ppm (3m; about 64 H)
1.9-2.1 ppm (m; 4 H)
2.1-2.4 ppm (m; 4 H)
3.3-3.5 ppm (m, 2 H)
3.7-3.9 ppm (t, 4 H)
4.1-4.3 ppm (t; 4 H)
4.3-4.6 ppm (m; 2 H)
4.6-4.9 ppm (m; 2 H)
5.2-5.6 ppm (m; 4 H)

11. 337 g (1 mole) of 2-(11-hydroxy-8-heptadecenyl)-5-methyl-2-oxazoline (technical) and 125 g (0.5 mole) of 4,4'-diphenylmethane diisocyanate (DESMODUR ® M, Bayer AG) were heated with stirring to 80° C. in the absence of moisture until the reaction was complete (4 hours). The product solidified on cooling to form a solid wax-like product. The following structure was confirmed by an H-NMR spectrum:

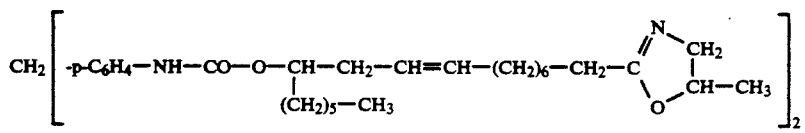

NMR (1% in CDCl₃, delta scale)
0.8-1.0 ppm (t; 6 H)
1.1-1.8 ppm (2m; about 46 H)
1.9-2.4 ppm (1m+2 d; 4+4+4 H)
3.25-3.45 ppm (q; 2 H)
3.8-4.0 ppm (m+s; 2+2 H)
4.5-4.75 ppm (m; 2 H)
4.75-4.95 ppm (m; 2 H)
5.2-5.6 ppm (m; 4 H)
6.7 ppm (s; 2 H)
7.0-7.4 ppm (2 d; 8H)

12. 351 g (1 mole) of 2-(11-hydroxy-8-heptadecenyl)-4,4-dimethyl-2-oxazoline (technical) and 125 g (0.5 mole) of 4,4'-diphenylmethane diisocyanate (DESMODUR ® M, Bayer AG) were heated with stirring to 80° C. in the absence of moisture until the reaction was complete (8 hours). After cooling, the product was a light yellow viscous liquid. The following structure of the product was confirmed by the H-NMR spectrum:

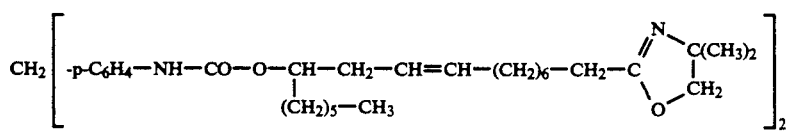

NMR (1% in CDCl₃, delta scale)
0.8-1.0 ppm (t; 6 H)
1.1-1.45 ppm (m; about 48 H)
1.45-1.6 ppm (m; 4 H)
1.9-2.4 ppm (3 m; 4+4+4 H)
3.85-3.95 ppm (2 s; 4+2 H)
4.8-4.9 ppm (m; 2 H)
5.2-5.6 ppm (m; 4 H)
6.6-6.7 ppm (s; 2 H)
7.0-7.4 ppm (2 d; 8 H)

13. A mixture of 351 g (1 mole) of 2-(11-hydroxy-8-heptadecenyl)-4,4-dimethyl-2-oxazoline (technical) and 131 g (0.5 mole) of 4,4'-dicyclohexylmethane diisocyanate (DESMODUR ® W, Bayer AG) was heated in the absence of moisture for 72 hours to 80° C. After cooling, the product was a yellowish viscous liquid. The structure of the product was confirmed by the H-NMR spectrum:

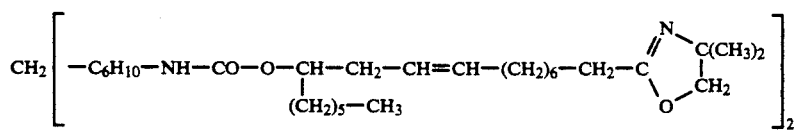

NMR (1% in CDCl₃, delta scale)
0.8-2.4 ppm (7 m; about 90 H)
3.3-3.8 ppm (2 m; 2 H)
3.9 ppm (s; 4 H)
4.3-4.85 ppm (2 m; 1+3 H)
5.2-5.6 ppm (m; 4 H)

14. A mixture of 157 g (1 mole) of 2-(5-hydroxypentyl)2-oxazoline and 111 g (0.5 mole) of isophorone diisocyanate (VEBA Chemie) was heated for 8 hours to 100° C. in the absence of moisture with addition of 130 mg dibutyl tin dilaurate. After cooling, the product was a highly viscous colorless substance. The structure of the product was confirmed by the H-NMR spectrum:

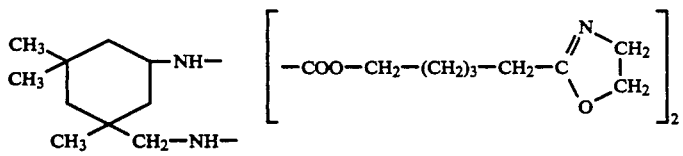

NMR (1% in CDCl₃, delta scale)
0.5–1.9 ppm (3 m; about 27 H)
2.1–2.4 ppm (t; 4 H)
2.8–3.0 ppm (d; 2 H)
3.1–3.55 ppm (2 m; 1 H)
3.7–3.9 ppm (t; 4 H)
3.9–4.1 ppm (m; 4 H)
4.1–4.3 ppm (t; 4 H)
4.4–5.0 ppm (2 m; 2 H)

15. Example 14 was repeated with addition of 460 g 2-nonyl-2-oxazoline as solvent. The mixture of mono- and bis-oxazoline obtained was a colorless solution of low viscosity. The H-NMR accorded with that of a mixture of the mono-oxazoline with the bis-oxazoline in 3.7–3.9 ppm (t; 4 H)
4.1–4.3 ppm (t; 4 H)
4.55–4.75 ppm (m; 2 H)
5.05 ppm (s; 2 H)
5.2–5.6 ppm (m; 4 H)
7.2–7.5 ppm (2 m; 3+1 H)

17. A mixture of 157 g (1 mole) of 2-(5-hydroxypentyl)2-oxazoline and 122 g (0.5 mole) of m-tetramethyl xylylene diisocyanate (m-TMXDI ®; Cyanamid) in 395 g 2-heptyl-2-oxazoline as solvent was heated for 72 hours to 80° C. in the absence of moisture. After cooling, the mixture of mono- and bis-oxazoline was a pale yellowish solution of low viscosity. The H-NMR spectrum corresponded to that of a mixture of the mono- and bis-oxazoline in an equivalent ratio of 7:3 with the following structure for the bis-oxazoline:

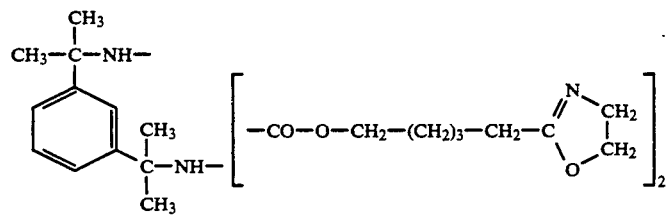

an equivalent ratio of 7:3.

16. A mixture of 323 g (1 mole) of 2-(11-hydroxy-8-heptadecenyl)-2-oxazoline with 122 g (0.5 mole) m-tetramethyl xylylene diisocyanate (m-TMXDI ®; Cyanamid) was stirred for hours at 80° C. in the absence of moisture. After cooling, the product was a yellowish viscous liquid.

The structure of the product was confirmed by the H-NMR spectrum:

NMR (1% in CDCl₃, delta scale)
0.8–0.95 ppm (t; about 21 H)
1.15–1.8 ppm (2 m; about 106 H)
2.15–2.4 ppm (t; about 20 H)
3.7–3.9 ppm (t; about 20 H)
4.1–4.3 ppm (t; about 20 H)
5.1–5.3 ppm (2 m; 3 H)
7.2–7.5 ppm (2 m; 4.5+1.5 H)

18. 325 g (1 mole) of 2-(11-hydroxyheptadecyl)-2-

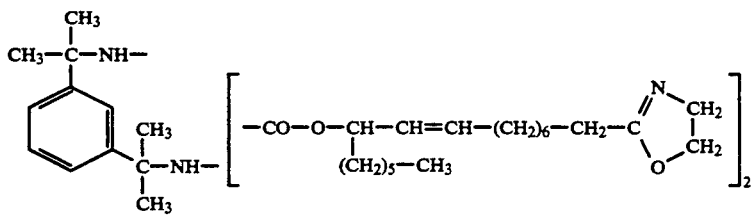

NMR (1% in CDCl₃, delta scale)
0.8–0.9 ppm (t; 6 H)
1.1–1.75 ppm (mm; about 52 H)
85–2.15 ppm (m; 4 H)
2.15–2.4 ppm (t; 8 H)

oxazoline and 111 g (0.5 mole) of isophorone diisocyanate (VEBA Chemie) were heated for 8 hours to 100° C. in the absence of moisture with addition of 220 mg dibutyl tin dilaurate. The product solidified on cooling to form a colorless wax-like paste. The structure of the product was confirmed by the H-NMR spectrum:

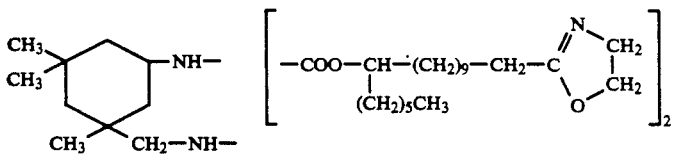

H-NMR (1% in CDCl₃, delta scale)
0.8–2.0 ppm (6 m; about 77 H)
2.2–2.3 ppm (t; 4 H)
2.85–2.95 ppm (d; 2 H)
3.2–3.5 ppm (m; 1 H)
3.7–3.9 ppm (t; 4 H)
4.1–4.3 ppm (t; 4 H)
4.35–4.5 ppm (m; about 2 H)
4.6–4.8 ppm (m; 2 H)

19. 325 g (1 mole) of 2-(11-hydroxyheptadecyl)-2-oxazoline and 131 g (0.5 mole) of 4,4′-dicyclohexylmethane diisocyanate (DESMODUR® W, Bayer AG) were heated for 8 hours to 100° C. in the absence of moisture with addition of 230 mg of dibutyl tin dilaurate. The product solidified on cooling to form a wax-like solid. The structure of the product was confirmed by the H-NMR spectrum:

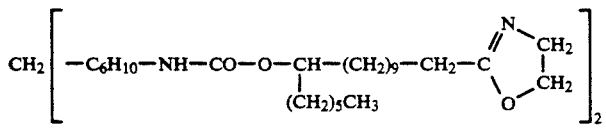

NMR (1% in CDCl₃, delta scale)
0.8–0.95 ppm (t; 6 H)
0.95–2.1 ppm (5 m; about 76 H)
2.15–2.35 ppm (t; 4 H)
3.25–3.65 ppm (m; 2 H)
3.7–3.9 ppm (t; 4 H)
4.1–4.3 ppm (t; 4 H)
4.3–4.55 ppm (m; about 2 H)
4.6–4.9 ppm (m; 4 H)

What is claimed is:

1. Bis-, tris-, and tetrakis-iminoethers corresponding to formula I:

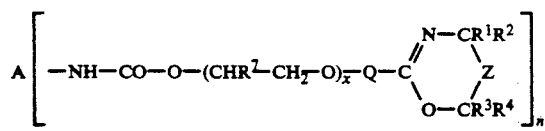

in which A is an aliphatic, aromatic or araliphatic group containing 4 to 40 carbon atoms and n free valencies at various carbon atoms; x has a value from 0 to 40; n has a value of 2, 3 or 4; Z is either a direct bond or the group $CR^5R^6$; the substituents $R^1$ to $R^6$ independently of one another are H, alkyl or aryl having up 8 carbon atoms; the substituent $R^7$ is selected from the group consisting of hydrogen, methyl and ethyl and Q is a phenylene group, which may be substituted by one or two methyl groups, or the group —CHR—M—, where R is selected from the group consisting of H, alkyl or alkenyl and M is selected from the group consisting of alkylene, alkenylene, arylene and alkarylene, and the parts R and M of the molecule independently of one another have 0 to 12 carbon atoms and may be substituted by a $C_{1-3}$ alkoxy group.

2. Bis-, tris-, and tetrakis-iminoethers as claimed in claim 1, in which Q in formula I is the group —CHR—M—.

3. Bis-, tris- or tetrakis-iminoethers as claimed in claim 2, in which at least one part —O—CHR—M— of the molecule is derived from the 11-hydroxyheptadecenyl moiety.

4. Bis-iminoethers as claimed in claim 1, in which n in formula I has the value 2.

5. Bis-iminoethers as claimed in claim 4, in which A is selected from the group consisting of 1,6-hexamethylene; 2,4-tolylene; 4,4′-methanediphenyl; 2,4′-methanediphenyl, 4,4′-methanedicyclohexyl, m-tetramethyl xylylene and isophoronylene.

6. Bis-, tris-, and tetrakis-iminoethers as claimed in claim 1, in which at least four of the substituents $R^1$ to $R^6$ are hydrogen atoms and the others consist of $C_{1-3}$ alkyl.

7. Bis-, tris-, and tetrakis-iminoethers as claimed in claim 1, in which x has a value in the range of 0 to 10.

8. Bis-, tris-, and tetrakis-iminoethers as claimed in claim 1, in which Z in formula I is a direct bond.

9. Bis-, tris-, and tetrakis-iminoethers as claimed in claim 8, in which $R^1$ is a methyl group and the substituents $R^2$ to $R^4$ are hydrogen.

10. Bis-, tris-, and tetrakis-iminoethers as claimed in claim 8, in which $R^1$ and $R^2$ are methyl groups and $R^3$ and $R^4$ are hydrogen.

11. Bis-, tris-, and tetrakis-iminoethers as claimed in claim 8, in which $R^3$ is selected from the group consisting of methyl, ethyl and phenyl and the substitutents $R^1$, $R^2$ and $R^4$ are hydrogen.

12. Bis-, tris-, and tetrakis-iminoether as claimed in claim 1, in which x has the value 0 or 1.

13. Bis-, tris-, and tetrakis-iminoethers as claimed in claim 7, in which Z in formula I is a direct bond.

14. Bis-, tris-, and tetrakis-iminoethers as claimed in claim 13, in which $R^1$ is a methyl group and the substitutents $R^2$ to $R^4$ are hydrogen.

15. Bis-, tris-, and tetrakis-iminoethers as claimed in claim 13, in which $R^1$ and $R^2$ are methyl groups and $R^3$ and $R^4$ are hydrogen.

16. Bis-, tris-, and tetrakis-iminoethers as claimed in claim 13, in which $R^3$ is selected from the group consisting of methyl, ethyl and phenyl and the substituents $R^1$, $R^2$ and $R^4$ are hydrogen.

17. Bis-, tris-, and tetrakis-iminoethers as claimed in claim 6, in which Z in formula I is a direct bond.

18. Bis-iminoethers as claimed in claim 5, in which Z in formula I is a direct bond.

19. Bis-iminoethers as claimed in claim 4, in which Z in formula I is a direct bond.

* * * * *